United States Patent
Fukuda et al.

(10) Patent No.: US 10,591,459 B2
(45) Date of Patent: Mar. 17, 2020

(54) MEASURING APPARATUS AND MEASURING METHOD

(71) Applicant: ARKRAY, Inc., Kyoto (JP)

(72) Inventors: Kazuo Fukuda, Kyoto (JP); Hirokazu Matsuda, Kyoto (JP); Akiko Okami, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 417 days.

(21) Appl. No.: 14/264,212

(22) Filed: Apr. 29, 2014

(65) Prior Publication Data

US 2014/0326037 A1  Nov. 6, 2014

(30) Foreign Application Priority Data

May 2, 2013 (JP) ................................. 2013-097067
Apr. 18, 2014 (JP) ................................. 2014-086658

(51) Int. Cl.
*G01N 33/49* (2006.01)
*G01N 27/327* (2006.01)

(52) U.S. Cl.
CPC ......... *G01N 33/49* (2013.01); *G01N 27/3273* (2013.01); *G01N 27/3274* (2013.01)

(58) Field of Classification Search
CPC .......................... G01N 33/49; G01N 27/3273
(Continued)

(56) References Cited

U.S. PATENT DOCUMENTS 7,407,811 B2    8/2008  Burke et al.
2007/0131565 A1  6/2007  Fujiwara et al.
(Continued)

FOREIGN PATENT DOCUMENTS

CN        1886651 A    12/2006
CN      101842695 A     9/2010
(Continued)

OTHER PUBLICATIONS

Office Action issued in corresponding Chinese Patent Application No. 201410185202.8 dated Jul. 4, 2016.
(Continued)

*Primary Examiner* — John Fitzgerald
*Assistant Examiner* — Rodney T Frank
(74) *Attorney, Agent, or Firm* — Morgan, Lewis & Bockius LLP

(57) ABSTRACT

Provided are a measuring apparatus and method for obtaining a measurement value from a response to a signal applied to a sample, wherein the measuring apparatus includes a first measuring unit that measures a first electric response to a first signal that is input to a first pair of electrodes that can come into contact with a sample, a second measuring unit that measures a second electric response to a second signal that is input to a second pair of electrodes that can come into contact with the sample, the second signal changing its value from a first level to a second level and thereafter maintaining the second level for a certain period of time, as a peak value of a response signal with respect to the change in the second signal, and a control unit that corrects a value indicating the amount of a measuring target component of the sample, the value being obtained from the first electric response, based on the peak value of the response signal.

8 Claims, 11 Drawing Sheets

(58) Field of Classification Search
USPC .................................................. 73/1.73, 48
See application file for complete search history.

(56) References Cited

U.S. PATENT DOCUMENTS

| | | | |
|---|---|---|---|
| 2008/0000780 A1 | 1/2008 | Tonks | |
| 2010/0327886 A1* | 12/2010 | Nakamura | G01N 27/3274 324/692 |
| 2011/0139634 A1 | 6/2011 | Chou et al. | |
| 2016/0376626 A1* | 12/2016 | Uchiyama | C12Q 1/006 205/777.5 |

FOREIGN PATENT DOCUMENTS

| | | |
|---|---|---|
| CN | 101918822 A | 12/2010 |
| EP | 0537761 A2 | 4/1993 |
| EP | 2211169 A1 | 7/2010 |
| EP | 2261646 A1 | 12/2010 |
| JP | 2005-147990 A | 6/2005 |
| KR | 10-2010-0101591 A | 9/2010 |
| TW | 200940983 A1 | 10/2009 |
| TW | 201120444 A1 | 6/2011 |
| WO | 2005/054840 A1 | 6/2005 |

OTHER PUBLICATIONS

Office Action issued in corresponding Korean Patent Application No. 10-2014-0052702 dated Jul. 14, 2016.
Office Action issued in corresponding Japanese Patent Application No. 2014-086658 dated May 7, 2015.
Extended European Search Report issued in corresponding European Patent Application No. 14166164.5 dated Jul. 29, 2014.
Office Action issued in corresponding Taiwanese Patent Application No. 103115691 dated Feb. 17, 2016.
Office Action issued in corresponding Chinese Patent Application No. 201410185202.8 dated Mar. 22, 2017.

* cited by examiner

MEASURING APPARATUS AND MEASURING METHOD

BACKGROUND OF THE INVENTION

1. Field of the Invention

The present invention relates to a technology for measuring a component contained in a sample based on a response obtained by applying a signal to the sample.

2. Description of Related Art

Conventionally, apparatuses and methods for obtaining information on a medically significant component in a biological sample, such as blood, based on a response that is obtained by applying a signal to the sample have been developed. For example, U.S. Pat. No. 7,407,811 discloses a method including determining a hematocrit value of a blood sample using a response to an AC signal that is applied to the blood sample and at a temperature of the blood sample, combining the hematocrit value and the temperature with a response to a DC signal that is applied to the blood sample, and displaying a glucose concentration of the blood sample. This method achieves accurate measurement of blood glucose without the error that is caused by variations in the temperature and the hematocrit value of the blood sample. Note that according to this method, the response to the AC signal is measured as an admittance value or magnitude and phase angle information.

US 2011/0139634A1 discloses a measuring instrument that supplies a signal having an AC component and a signal having a DC component simultaneously and respectively to two pairs of electrodes having separate reaction zones. This measuring instrument achieves more accurate measurement by acquiring an analyte concentration and a hematocrit level respectively in the separate zones.

SUMMARY OF THE INVENTION

An object of the disclosure of the present application is to provide a more simplified apparatus and method for obtaining a measurement value from a response to a signal that is applied to a sample.

A measuring method disclosed in the present application is a method for measuring a measuring target component of a sample, the method including the steps of applying a first signal to the sample, measuring a first electric response of the sample to the first signal, applying a second signal to the sample, the second signal changing its value from a first level to a second level and thereafter maintaining the second level for a certain period of time, measuring a second electric response of the sample to the second signal as a peak value of a response signal with respect to the change in the second signal, and correcting a value indicating an amount of the measuring target component of the sample, the value being obtained from the first electric response, based on the peak value of the response signal.

According to the disclosure of the present application, it is possible to provide a more simplified apparatus and method for obtaining a measurement value from a response to a signal that is applied to a sample.

DETAILED DESCRIPTION OF THE INVENTION

Figure 1:
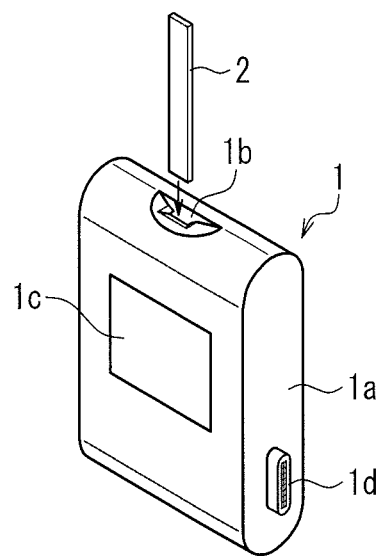
FIG. 1 is a perspective view for explaining a measuring apparatus according to Embodiment 1 and an analytical device.

According to the conventional technologies disclosed in U.S. Pat. No. 7,407,811 and US 2011/0139634A1 described above, the admittance or the phase angle is used as the response to the AC signal in measuring the hematocrit value to be used for the correction of the glucose value. Thus, systems for measuring them are likely to be complicated. Also, according to the above-described conventional technologies, since the hematocrit value is judged by means of a plurality of input waves, the time required for measurement is prolonged.

A measuring method according to an embodiment of the invention measures a measuring target component of a sample, the method including the steps of applying a first signal to the sample, measuring a first electric response of the sample to the first signal, applying a second signal to the sample, the second signal changing its value from a first level to a second level and thereafter maintaining the second level for a certain period of time, measuring a second electric response of the sample to the second signal as a peak value of a response signal with respect to the change in the second signal, and correcting a value indicating an amount of the measuring target component of the sample, the value being obtained from the first electric response, based on the peak value of the response signal.

A measuring apparatus according to an embodiment of the invention is a measuring apparatus including a first measuring unit that measures a first electric response to a first signal that is input to a first pair of electrodes that can come into contact with a sample, a second measuring unit that measures a second electric response to a second signal that is input to a second pair of electrodes that can come into contact with the sample, the second signal changing its value from a first level to a second level and thereafter maintaining the second level for a certain period of time, as a peak value of a response signal with respect to the change in the second signal, and a control unit that corrects a value indicating an amount of a measuring target component of the sample, the value being obtained from the first electric response, based on the peak value of the response signal.

According to the measuring method and the measuring apparatus described above, a signal that changes its value from a first level to a second level and thereafter maintains the second level for a certain period of time is applied to the sample as the second signal. The peak value of the response signal is measured as the second electric response to the second signal. Here, the value can be obtained by simple processing of measuring the peak value of the response signal. Then, the value indicating the amount of the measuring target component, the value being obtained from the first electric response, is corrected based on the peak value. Thus, the measurement accuracy can be improved with simple processing and configuration. That is to say, the measuring method and the measuring apparatus can be simplified.

For example, applying AC signals of a plurality of frequencies or acquiring admittance, phase angle information, etc. as a response to an AC signal in order to obtain a correction value for improving the measurement accuracy complicates the configuration of the apparatus and the signal processing method. However, according to the measuring apparatus and the measuring method described above, such a complicated configuration and processing are unnecessary, and therefore, the accuracy can be improved with a simple configuration and processing.

A measuring method according to another embodiment of the invention is a measuring method for measuring a hematocrit value of a blood sample, the method including the steps of applying a signal to a pair of electrodes that can come into contact with the blood sample, the signal changing its value from a first level to a second level and thereafter maintaining the second level for a certain period of time, measuring an electric response of the blood sample to the signal as a peak value of a response signal with respect to the change in the signal, and calculating the hematocrit value of the blood sample from the peak value by a processor.

A measuring apparatus according to another embodiment of the invention is a measuring apparatus for measuring a hematocrit value of a blood sample, including a measuring unit that measures an electric response to a signal that is input to a pair of electrodes that can come into contact with the blood sample, the signal changing its value from a first level to a second level and thereafter maintaining the second level for a certain period of time, as a peak value of a response signal with respect to the change in the signal, and a control unit that calculates the hematocrit value of the blood sample from the peak value.

According to the measuring method and the measuring apparatus described above, the hematocrit value can be obtained by simple processing of measuring the peak value of the response signal. Therefore, the measuring apparatus and measuring method for measuring a hematocrit value in a blood sample can be simplified.

In the above-described embodiments, it is possible that the second signal or the signal that is input to the pair of electrodes contains a rectangular wave or trapezoidal wave component as a waveform in which the second signal or the signal that is input to the pair of electrodes changes its value from the first level to the second level and thereafter maintains the second level for a certain period of time. Thus, the waveform of the signal to be applied to the sample can be made simple, and the accuracy of the value to be obtained from the peak value of the response signal can be improved.

In the above-described embodiments, it is possible that a time period for which the first signal is applied and a time period for which the second signal is applied are not the same. Thus, the necessity to process the response to the first signal and the response to the second signal at the same time is eliminated, and the apparatus and the processing can be simplified even more.

In the above-described embodiments, it is possible that the first signal is applied to the sample in a state in which the sample is reacted with a reagent, and the second signal is applied to the sample in a state in which the sample is not reacted with the reagent. That is to say, a configuration can be adopted in which the first measuring unit measures the first electric response to the first signal that is applied to the sample in the state in which the sample is reacted with the reagent, and the second measuring unit measures the second electric response to the second signal that is applied to the sample in a state in which the sample is not reacted with the reagent. For example, a configuration can be adopted in which the first measuring unit measures the first electric response to the first signal that is input to the first pair of electrodes that can come into contact with the sample in a state in which the sample is reacted with the reagent, that is, the first pair of electrodes on which the reagent is provided, and the second measuring unit measures the second electric response to the second signal that is input to the second pair of electrodes that can come into contact with the sample in a state in which the sample is not reacted with the reagent, that is, the second pair of electrodes on which no reagent is provided.

Thus, the measurement of the value indicating the amount of the measuring target component and the measurement of the value that is used for correction can be independently performed using separate steps or separate electrodes. As a result, the measurement accuracy can be improved even more.

The time it takes for the second signal or the signal that is input to the pair of electrodes to change its value from the first level to the second level can be set at 30 µs or less. Thus, the change from the first level to the second level can be made quicker, and the measurement accuracy can be improved. Note that the measurement accuracy can be improved further by setting the time at 7 µs or less. Moreover, the measurement accuracy can be improved even further by setting the time at 2 µs or less.

Note that the measuring apparatus may further include an analytical device having the first pair of electrodes which are located in a flow path of the sample and on which the reagent is provided, and the second pair of electrodes which are located in the flow path and on which the reagent is not provided.

Hereinafter, preferred embodiments of a measuring apparatus and a measuring method according to the invention will be described with reference to the drawings. Note that in the following description, a case where the invention is applied to a blood glucose meter is taken as an example. Also, the dimensions of constituent members shown in the drawings are exemplary representations of the actual dimensions of the constituent members, the actual dimensional ratios of the constituent members, etc.

Embodiment 1

Example of Configuration of System

FIG. 1 is a perspective view for explaining a measuring apparatus according to Embodiment 1 and an analytical device. This embodiment exemplifies a case where the measuring apparatus is used as a portable blood glucose meter, for example. Referring to FIG. 1, a portable blood glucose meter 1 serving as the measuring apparatus, and an analytical device 2 that is configured to be removably attached to the blood glucose meter 1 are provided. The analytical device 2 is adapted so that blood (a sample) of a patient can be deposited on (introduced into) the analytical device 2. The analytical device 2 is configured to have the function of a (bio)sensor for detecting the blood glucose level (glucose level) in blood. The blood glucose meter shown in FIG. 1 can be used as, for example, a blood glucose meter such as a portable blood glucose monitoring (BGM) device or a meter for self-monitoring of blood glucose (SMBG).

The blood glucose meter 1 includes a main body 1a, and an insertion port 1b into which the analytical device 2 having the shape of a rectangular strip can be inserted is formed in the main body 1a. Also, a control unit that may be configured by a microprocessor, for example, and that controls various units of the blood glucose meter 1 is provided in the main body 1a. The main body 1a also includes a measurement unit that supplies a predetermined voltage signal to the analytical device 2, receives a voltage signal indicating the measurement result from the analytical device 2, performs an analog-to-digital conversion of the received voltage signal, and generates measurement data indicating the measured value, and a recording unit that records the measurement data obtained by the measurement unit. The above-described control unit causes the measurement data obtained by the measurement unit to be recorded in the recording unit in association with the measuring time, a patient ID, etc.

Also, a display screen 1c on which the measurement data is displayed and a connector 1d for data communication with an external apparatus are provided on the main body 1a. The connector 1d is configured to send/receive data such as the measurement data, measuring time, patient ID, etc. to/from a portable apparatus such as a smartphone, a personal computer, or the like serving as the external apparatus. That is to say, the blood glucose meter 1 is configured to be able to transfer the measurement data and the measuring time to the external apparatus via the connector 1d, and receive the patient ID, etc. from the external apparatus via the connector 1d and associate the received patient ID, etc. with the measurement data, etc.

Note that instead of the configuration described above, it is also possible to adopt a configuration in which the measurement unit is provided in an end portion of the analytical device 2, and the measurement data is generated by the analytical device 2. Moreover, the main body 1a of the blood glucose meter 1 may also be equipped with a user interface including an input unit such as a keypad or a touch panel through which a user such as a patient inputs data. Moreover, it is also possible to adopt a configuration in which the display screen 1c, the recording unit, etc. are provided on an external apparatus that can be connected to the main body 1a, instead of being provided on the main body 1a.

Example of Configuration of Measuring Apparatus

Figure 2:
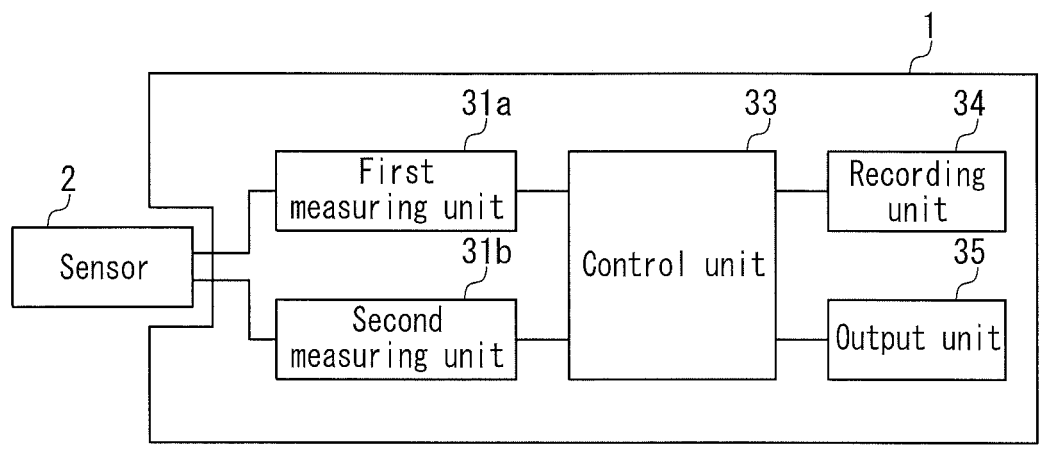
FIG. 2 is a block diagram showing an example of the configuration of a blood glucose meter 1 serving as an example of the measuring apparatus.

FIG. 2 is a block diagram showing an example of the configuration of the blood glucose meter 1, which is an example of the measuring apparatus. In the example shown in FIG. 2, the sensor (analytical device) 2 includes two pairs of electrodes (first pair of electrodes and second pair of electrodes) (not shown) that are provided in a flow path of the sample. The blood glucose meter 1 includes a first measuring unit 31a, a second measuring unit 31b, a control unit 33, a recording unit 34, and an output unit 35. The first measuring unit 31a measures a first electric response to a first signal that is input to the first pair of electrodes that can come into contact with the sample. The second measuring unit 31b measures a second electric response to a second signal that is input to the second pair of electrodes that can come into contact with the sample. Here, the second signal contains a waveform in which the value of the second signal changes from a first level to a second level and thereafter remains at the second level for a certain period of time. The second measuring unit 31b measures the second electric response to this second signal as a peak value of a response signal with respect to the change in the second signal. The control unit 33 corrects a value indicating the amount of a measuring target component of the sample, the value being obtained from the first electric response, based on the peak value of the response signal, which is measured by the second measuring unit 31b. The corrected value indicating the amount of the measuring target component is, for example, recorded in the recording unit 34 and displayed on the display screen 1c by the output unit 35.

The configuration of the measuring apparatus is not limited to the above-described portable measuring apparatus. For example, the measuring apparatus can also be configured such that the measuring unit is connected to a mobile telephone, a smartphone, a game console, a personal computer, a server computer, or the like. In this case, the control unit 33 can be configured by a computer of an apparatus to which the measuring unit can be connected.

The control unit 33 can be realized by a processor included in a computer of the measuring apparatus executing a predetermined program. For example, a microcontroller can be incorporated into the blood glucose meter 1. By way of example, such a microcontroller can be configured to include a core processor that constitutes the control unit 33. Note that programs that cause a computer to function as the control unit 33 and non-transitory recording media in which those programs are recorded are also included in embodiments of the invention. Furthermore, methods according to which a computer executes these programs are also included in embodiments of the invention.

In this embodiment, by way of example, a pair of glucose electrodes for measuring glucose in the sample are used as the first pair of electrodes of the sensor 2, and a pair of hematocrit electrodes for measuring the hematocrit of the sample are used as the second pair of electrodes. The first pair of electrodes and the second pair of electrodes as described above are formed as electrodes that are exposed in the flow path of the sample in the sensor 2. For example, a reagent, such as oxidoreductase and an electron transfer substance, is provided on the glucose electrodes. No such reagent is provided on the hematocrit electrodes.

The first measuring unit 31a, based on an instruction from the control unit 33, applies, for example, a DC signal as the first signal to the glucose electrodes that are in contact with the sample in a state in which the sample is reacted with the reagent, and measures a response signal as the first electric response. The control unit 33 can determine a value indicating a glucose concentration based on the response signal value.

The second measuring unit 31b, based on an instruction from the control unit 33, applies, for example, a pulse signal having a rectangular or trapezoidal waveform as the second signal to the hematocrit electrodes that are in contact with the sample in a state in which the sample is not reacted with the reagent. The second measuring unit 31b measures a peak value of a response signal with respect to a change in the signal level of the second signal, for example, a rising edge of the pulse. In this manner, measuring a peak value of the response signal with respect to a change in the level of the input signal makes it possible for the control unit 33 to determine a value indicating the amount of hematocrit using the peak value. That is to say, it is possible to calculate a hematocrit value by measuring a peak current that is caused by a sharp change in the input signal. Furthermore, the control unit 33 can correct the value indicating the concentration of glucose, which is obtained from the first response signal value to the first signal, using the hematocrit value.

Figure 3:
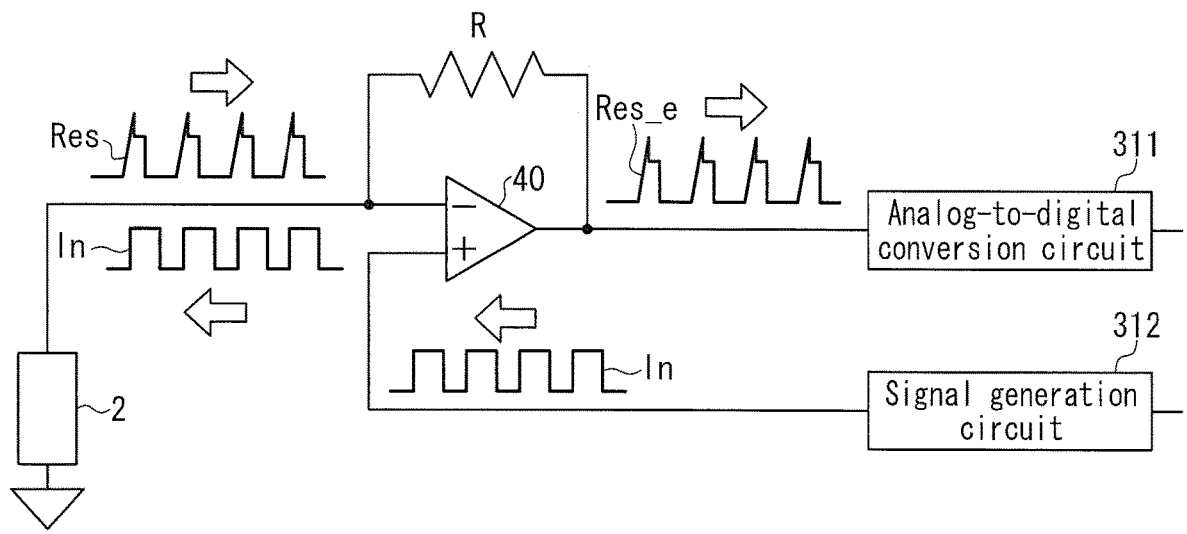
FIG. 3 is a diagram showing an example of the circuit configuration of a second measuring unit.

FIG. 3 is a diagram showing an example of the circuit configuration of the second measuring unit 31b. In the example shown in FIG. 3, a signal generation circuit 312 is connected to the positive terminal of an operational amplifier 40, and the second pair of electrodes of the sensor 2 are connected to the negative terminal. The output terminal of the operational amplifier 40 is connected to an analog-to-digital conversion circuit 311. A resistance R is connected between the negative terminal and the output terminal of the operational amplifier 40. In the example shown in FIG. 3, a pulse wave is input to the positive terminal of the operational amplifier 40 as an input signal In, and this pulse wave In (pulse voltage, for example) is input to the second pair of electrodes of the sensor 2. The second pair of electrodes are in contact with the sample, and a response current Res of the sample is input to the negative terminal side of the operational amplifier 40, converted into a voltage signal Res_e, and output from the output terminal side of the operational amplifier 40. The voltage signal Res_e is converted into a digital signal by the analog-to-digital conversion circuit 311 and output to the control unit 33. Note that a configuration in which the peak value is detected by a detection circuit (not shown) that is provided between the operational amplifier 40 and the analog-to-digital conversion circuit 311 may also adopted, or a configuration in which the peak value is calculated by the control unit 33 may also be adopted. The signal generation circuit 312 generates the input signal based on an instruction from the control unit 33.

In this manner, the second measuring unit 31b can apply a signal having a rising component and a waveform component that has a constant value after rising to the sample as the second signal. Then, the second measuring unit 31b can measure the second electric response of the sample, which has a rectangular wave or trapezoidal wave component, by means of the peak value of the response signal.

With regard to the peak value, for example, the greatest response signal value of response signal values that are detected within a certain period of time after the time point at which the level of the second signal has changed (e.g., the time point at which the pulse has risen) can be used as the peak value. Alternatively, it is also possible to use a circuit for holding a peak value of a response signal in a certain period of time and measure, as the peak value of the response signal, the value of a peak that is held in a certain period of time after, for example, the time when the level of the second signal has changed. The magnitude of the peak value can be detected as the difference between the level before the rising of the response signal value or the level at the time when the response signal value stabilizes at a certain value after the rising and the level at the peak. That is to say, a value relative to the level during a stable period before or after the change in the response signal value can be measured as the peak value.

The response signal value can be measured as a response current value or a response voltage value. By way of example, the above-described circuit shown in FIG. 3 is configured to apply a voltage signal to the pair of electrodes and thereby obtain an output of a peak top current as the response. Note that the peak value is not necessarily required to be exactly the value at the highest point that is reached by the response signal, and the greatest value of discrete values that are detected at predetermined intervals within a certain period of time can be used as the peak value.

In this embodiment, the peak value can be obtained if a response signal value with respect to at least one change in the level of the input signal can be detected. Accordingly, for example, a hematocrit value can be obtained in a short period of time. Note that it is also possible to successively input a plurality of pulses and acquire peak values of the response signal with respect to a plurality of changes in the signal level. In this case, for example, the accuracy of the peak value can also be improved by obtaining a representative value (e.g., mean value, etc.) of the plurality of peak values.

Figure 4:
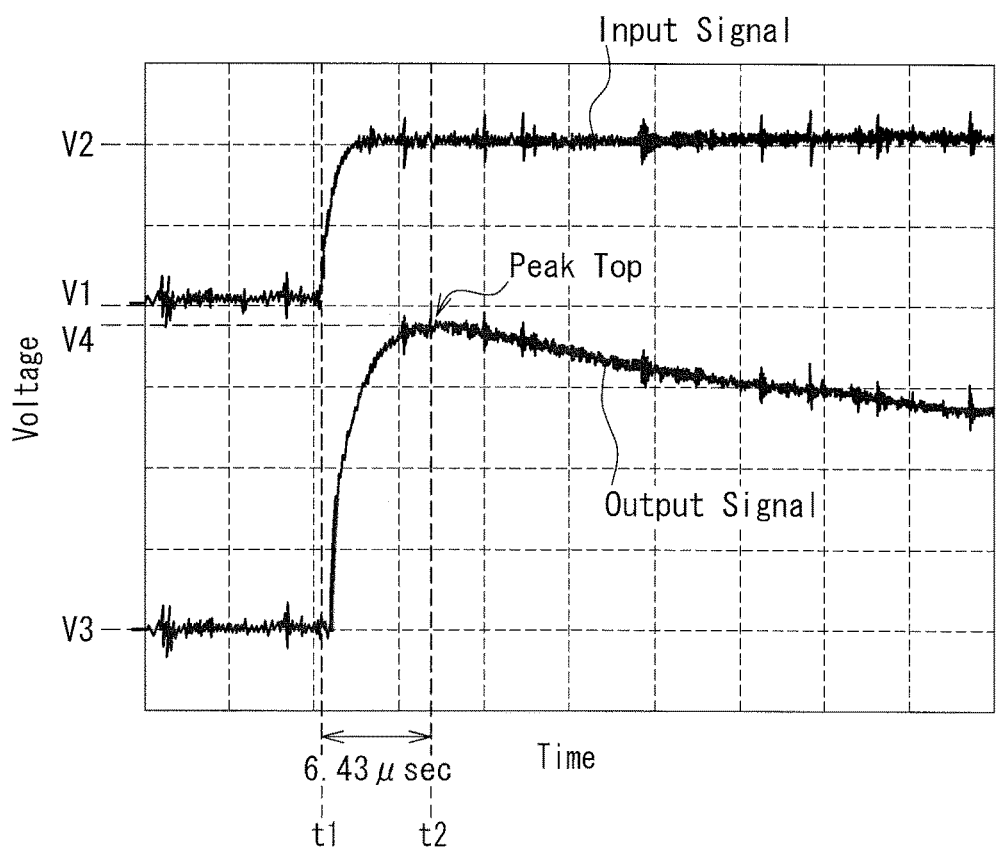
FIG. 4 is a graph showing an example of an input signal that is input to a second pair of electrodes and an output signal.

FIG. 4 is a graph showing an example of the input signal (second signal) "Input Signal" that is input to the second pair of electrodes of the sensor 2 and the output signal (second electric response signal) "Output Signal". In the graph shown in FIG. 4, the horizontal axis indicates time, and the vertical axis indicates voltage level. In the example shown in FIG. 4, when the voltage level of the input signal "Input Signal" changes from V1 to V2, the voltage level of the output signal also sharply changes from V3 to V4 and then gradually decreases. For example, here, the level of the output signal reaches the peak ("Peak Top") after a lapse of 6.43 μs from time point t1 at which the input signal has risen (i.e., has begun changing).

Figure 5:
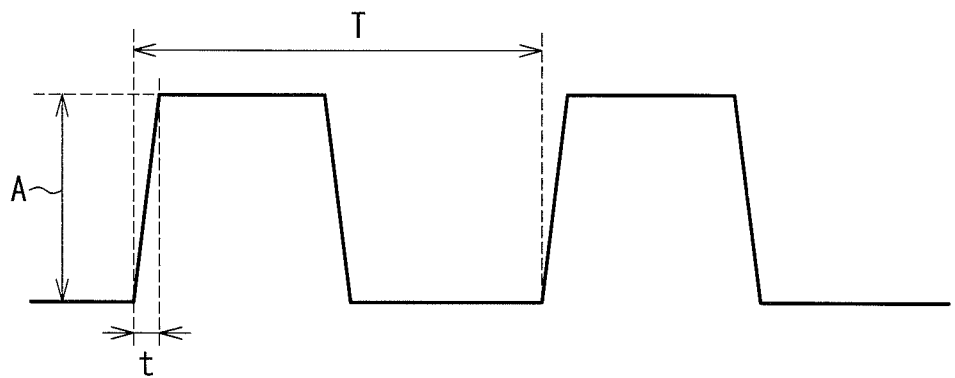
FIG. 5 is a diagram for explaining a form of the input signal (second signal).

FIG. 5 is a diagram for explaining a form of the input signal (second signal). FIG. 5 shows a voltage pulse wave as an example of the input signal. Here, the period T of the pulse wave, the potential difference A between the first level and the second level, and the rise time "t" (an example of the time it takes for the input signal to change from the first level to the second level) can be set as appropriate in accordance with the structure of the sensor 2, the environment of the measurement system, etc. For example, 1/T can be set at 1 to 500 [Hz], the rise time "t" can be set to be shorter than 30 μs, and the potential difference A can be set within a range of 50 to 1000 mV. Also, the hematocrit can be measured by applying a pulse wave signal up to a maximum of 0.2 seconds to the hematocrit electrodes as the input signal. Note that in the example shown in FIG. 5, the signal to be applied, that is, the input signal is represented by voltage; however, the input signal may also be represented by current. In other words, the input signal can be controlled by controlling the voltage to be applied to the hematocrit electrodes, or the input signal can be controlled by controlling the current.

In the example shown in FIG. 5, the signal has a waveform that rises from a level to a higher level, maintains the higher level for a certain period of time, and then returns to the initial level. In contrast, it is also possible to input a signal having a waveform that falls from a level to a lower level, maintains the lower level for a certain period of time, and then returns to the initial level. In this case, the peak value of a response signal with respect to the change in the signal from the initial level to the lower level or a response signal with respect to the change from the lower level to the initial level can be measured.

Figure 6:
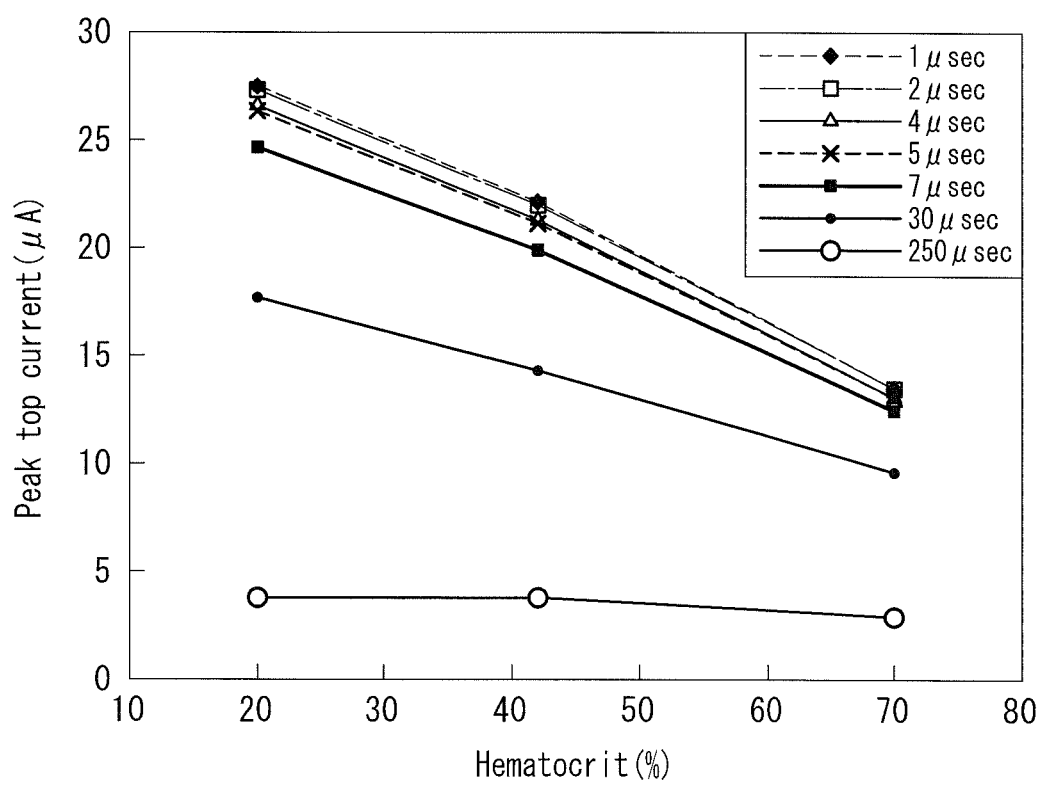
FIG. 6 is a graph showing a relationship between pulse rise time of the input signal and a peak value of a response signal.

The inventors of the invention found that the time it takes for the input signal to change its level (e.g., rise time) is important in order to generate the peak value of the response signal with high accuracy. FIG. 6 is a graph showing a relationship between the pulse rise time of the input signal and the peak value of the response signal. This graph shows that if, for example, the time it takes for the input signal to change from the first level to the second level is 30 μs or shorter than 30 μs, the peak value of the response signal can be generated with high accuracy. If this time is 7 μs or shorter than 7 μs, variations in the peak value of the response signal depending on the hematocrit value become more significant. This means that the peak value can be generated with high accuracy. Desirably, the magnitude of the peak value is increased by setting the time it takes for the input signal to change from the first level to the second level at 2 μs or shorter than 2 μs, so that the peak value of the response signal can be obtained with even higher accuracy.

Note that there is no limitation on the period of time for which the value of the input signal is maintained at the second level after changing from the first level to the second level. For example, the second level can be maintained for a period of time that is longer than the time it takes for the response signal to become stable at a certain value after reaching the peak with respect to the change in the input signal. In the case of the pulse wave shown in FIG. 5, the period of time after rising of a pulse until returning again to the initial level (i.e., the period of time for which the second level is maintained) can be set to be longer than the time it takes for the response signal to stop fluctuating after reaching its peak. Thus, the peak value can be reliably detected.

Also, the inventors of the invention found that in order to obtain the peak value, it is important that the signal level of the input signal change from a value to a different value in a short period of time, and the input signal is not necessarily required to be a pulse wave that repeats at a constant frequency and has a constant potential difference. For example, a signal having a stepwise waveform in which the signal level changes on the step-by-step basis at intervals can also be applied to the sample.

Figure 7:
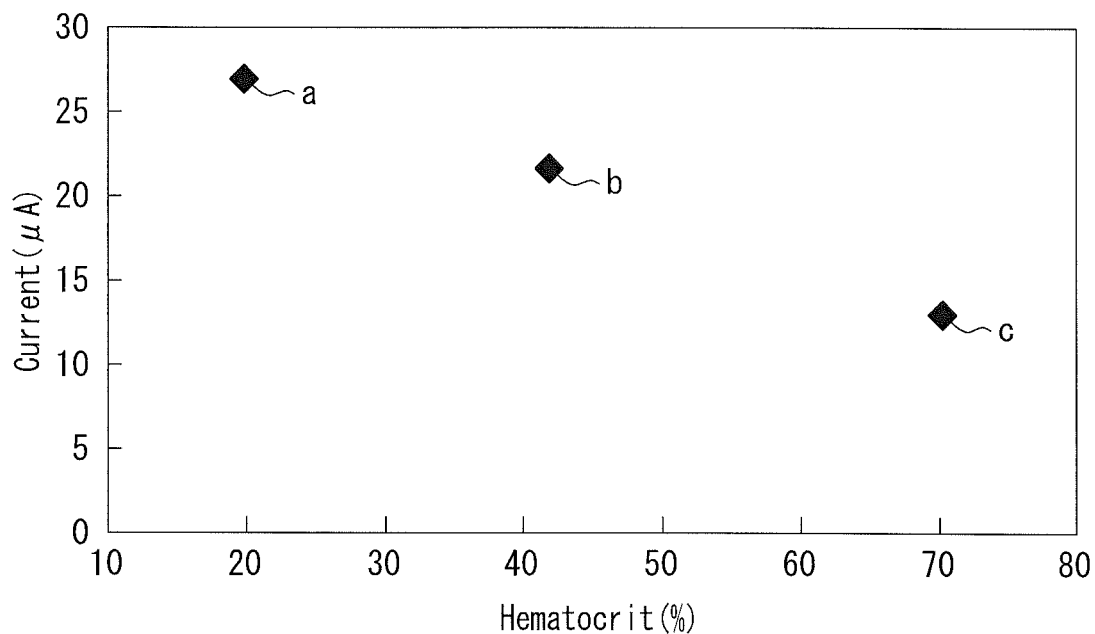
FIG. 7 is a graph showing an example in the case where samples of known hematocrit values are measured with the stepwise waveform shown in FIG. 8.
Figure 8:
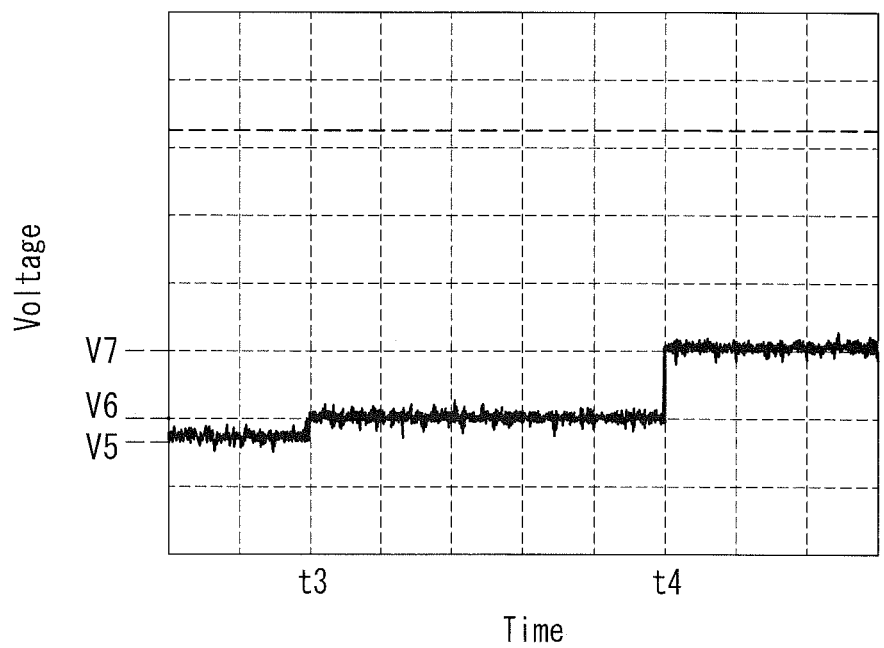
FIG. 8 is a graph showing an example of the input signal having a stepwise waveform.
Figure 9:
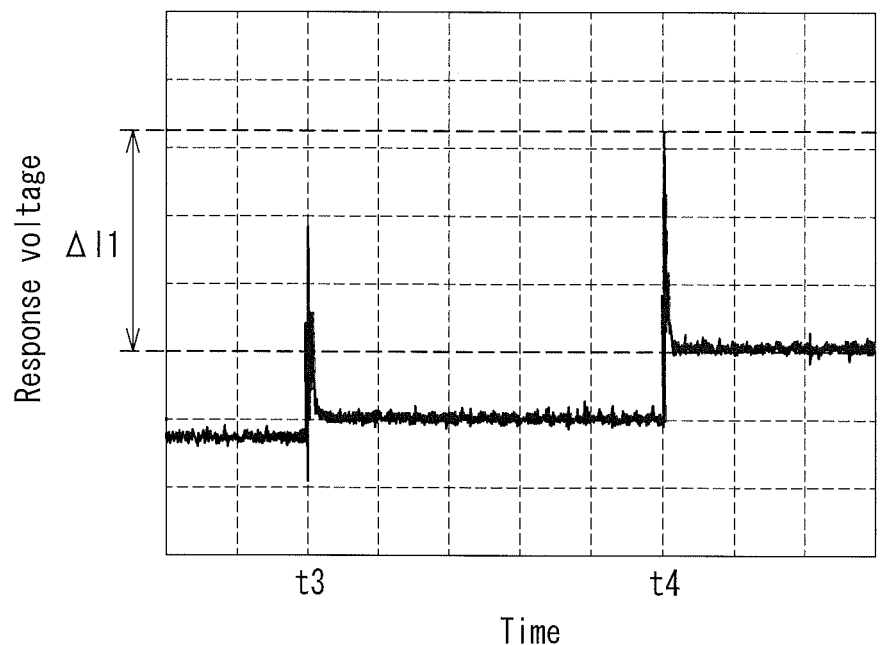
FIG. 9 is a graph showing an example of the response signal in the case where the input signal shown in FIG. 8 is applied to a sample having a hematocrit value of 20%.
Figure 10:
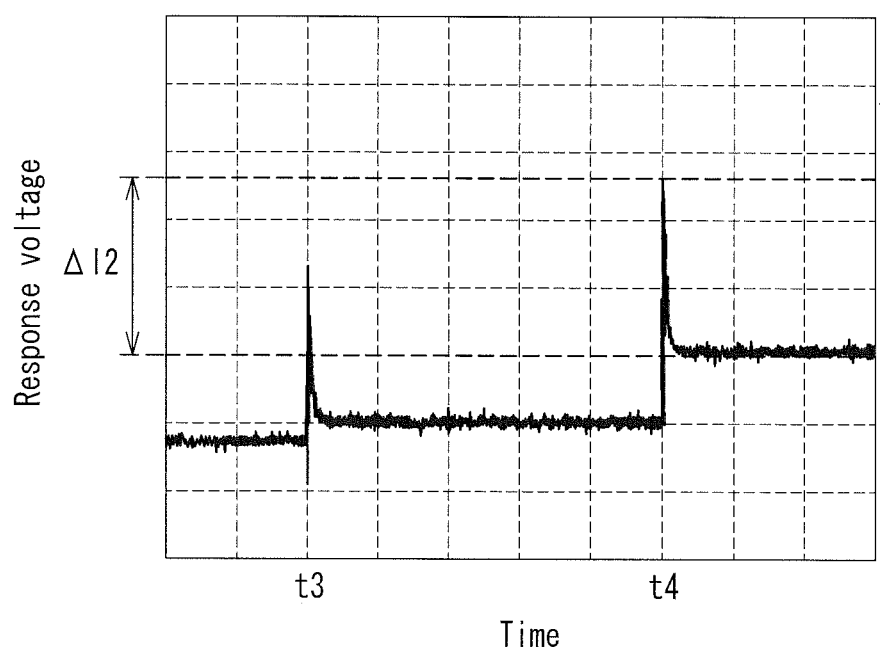
FIG. 10 is a graph showing an example of the response signal in the case where the input signal shown in FIG. 8 is applied to a sample having a hematocrit value of 40%.
Figure 11:
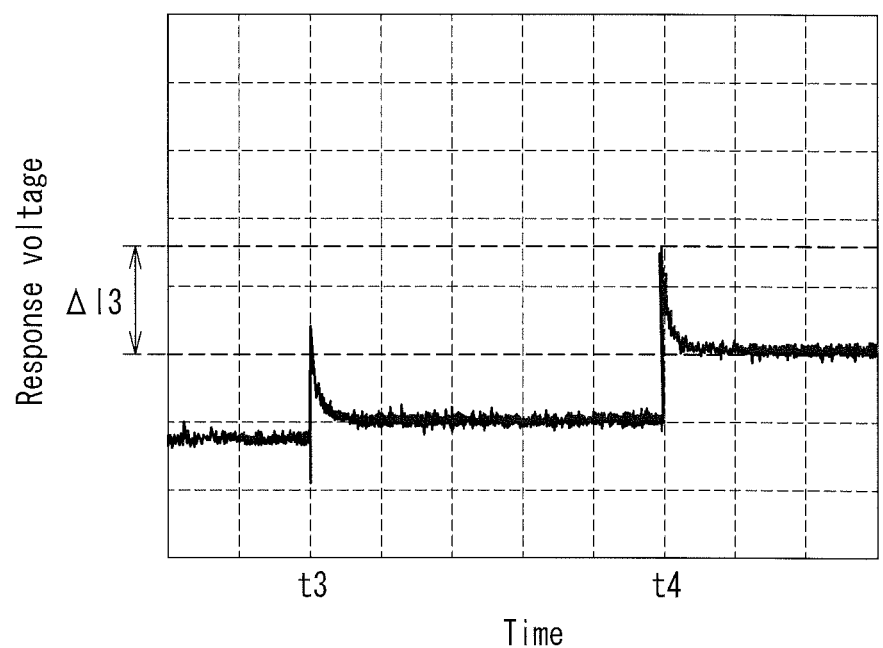
FIG. 11 is a graph showing an example of the response signal in the case where the input signal shown in FIG. 8 is applied to a sample having a hematocrit value of 70%.

FIG. 7 is a graph showing an example in the case where three types of samples of known hematocrit values are measured with a stepwise waveform shown in FIG. 8, in which the signal level increases on the step-by-step basis at time intervals. In the graph shown in FIG. 7, the vertical axis indicates peak values of response signals, and the horizontal axis indicates the amounts of hematocrit. The level of the input signal shown in FIG. 8 increases from V5 to V6 at time t3, then remains at V6, and increases from V6 to V7 at time t4. FIG. 9 is a graph showing an example of the response signal in the case where the input signal shown in FIG. 8 is applied to the sample (the hematocrit electrodes that are in contact with this sample) whose hematocrit value is 20%. In the case that is shown in FIG. 9, the peak value of the response signal with respect to the rising edge of the input signal at time t4 is measured as a difference ΔI1 between the rising peak top and the current value during the stable period that comes after the rising peak top. Similarly, FIG. 10 is a graph showing an example of the response signal in the case where the input signal shown in FIG. 8 is applied to the sample whose hematocrit value is 40%. In the example in FIG. 10, the peak value of the response signal with respect to the rising edge of the input signal at time t4 is measured as a difference ΔI2 between the peak top and the current value during the stable period that comes after the peak top. FIG. 11 is a graph showing an example of the response signal in the case where the input signal shown in FIG. 8 is applied to the sample whose hematocrit value is 70%. In the example in FIG. 11, the peak value of the response signal with respect to the rising edge of the input signal at time t4 is measured as a difference ΔI3 between the peak top and the current value during the stable period that comes after the peak top.

In FIG. 7, a plot "a" corresponds to the peak value ΔI1 that is detected based on the response signal with respect to the rising edge at time t4 in FIG. 9, a plot "b" corresponds to the peak value ΔI2 in FIG. 10, and a plot "c" corresponds to the peak value ΔI3 in FIG. 11.

Example of Operation

Figure 12:
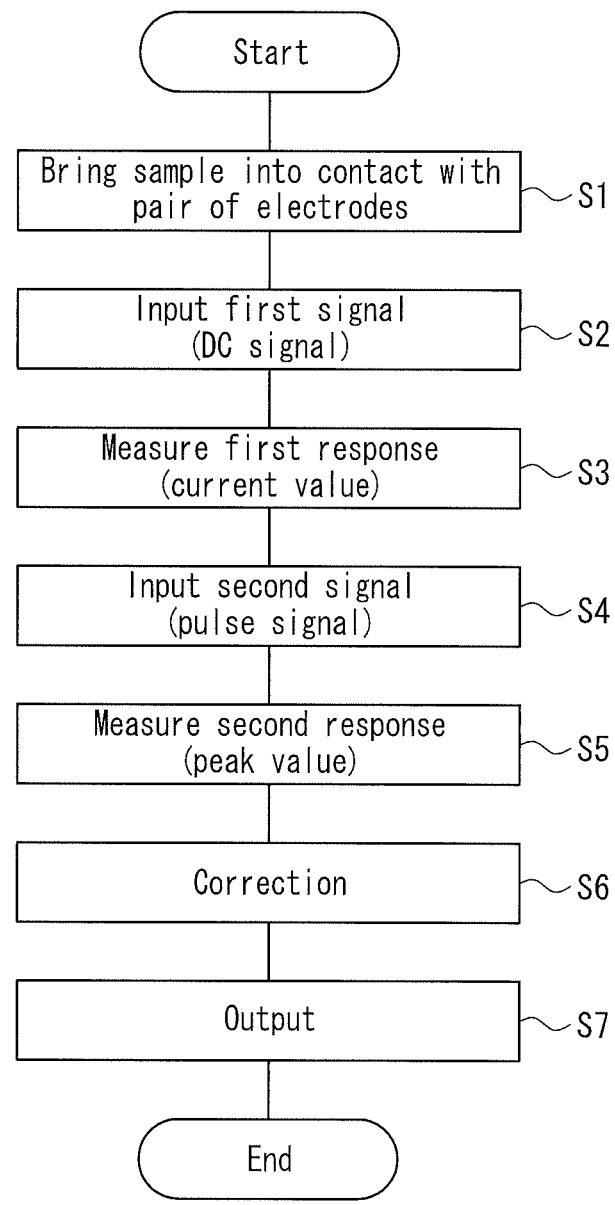
FIG. 12 is a flowchart illustrating an example of the operation of the measuring apparatus according to Embodiment 1.

FIG. 12 is a flowchart illustrating an example of the operation of the blood glucose meter 1 according to this embodiment. In the example shown in FIG. 12, measurement is started when the sample comes into contact with the pair of electrodes of the sensor 2 (step S1). For example, the blood glucose meter 1 can be configured to start when the sensor 2 is inserted into the sensor insertion port 1b. In this case, the control unit 33 can start measurement when it is detected that blood, which is the sample, is deposited on the inserted sensor 2.

The control unit 33 applies the first signal to the sample (step S2). For example, the control unit 33 instructs the first measuring unit 31a to apply a DC signal to the glucose electrodes as the first signal. The reagent is provided on the glucose electrodes in advance, and the sample in a state in which it is reacted with the reagent is in contact with the glucose electrodes.

The first measuring unit 31a measures the first electric response of the sample to the first signal (step S3). For example, the first measuring unit 31a can measure a response current with respect to the DC signal, perform an analog-to-digital conversion, and send the result to the control unit 33.

When the control unit 33 has acquired the first electric response of the sample to the first signal, the control unit 33 applies the second signal to the sample (step S4). For example, the control unit 33 instructs the second measuring unit 31b to apply a pulse signal to the hematocrit electrodes as the second signal. The sample in a state in which it is not reacted with the reagent is in contact with the hematocrit electrodes. The control unit 33 can instruct the second measuring unit 31b on, for example, the rise time, period, magnitude, duration of application, etc. of the pulse signal.

The second measuring unit 31b measures the second electric response of the sample to the second signal (step S5). For example, the second measuring unit 31b measures the peak value of the response signal with respect to a rising edge of the pulse of the second signal. The second measuring unit 31b may perform an analog-to-digital conversion of the peak value of the response signal and send the result to the control unit 33, or may perform an analog-to-digital conversion of values that are obtained by detecting the response signal at predetermined intervals (e.g., 0.1 μs) and send the result to the control unit 33.

The control unit 33 calculates a value (here, glucose concentration, by way of example) that indicates the amount of the measuring target component that is contained in the sample using the first electric response acquired in step S3 and the second electric response acquired in step S5 (step S6). Thus, a corrected value can be obtained by correcting the value indicating the amount of the measuring target component of the sample, which is obtained from the first electric response in step S3, based on the peak value of the response signal, which is obtained in step S5.

For example, in step S6, the control unit 33 can determine a value indicating the amount of hematocrit in the sample using the peak value of the response signal, which is acquired in step S5. For example, the hematocrit value can be obtained by an operation of substituting the peak value into a formula that has been recorded in advance. Alternatively, the control unit 33 can determine the hematocrit value by referring to a table in which the peak value of the response signal and the hematocrit value are recorded in association with each other. The control unit 33 can correct the glucose concentration value, which is obtained from the first electric response, using the thus determined hematocrit value. Note that the peak value (response current value or response voltage value) may also be used for the correction of the glucose value as it is, without being converted into the hematocrit value.

Now, an example of the calculation that is performed in conversion of the peak value of the response signal into the hematocrit value will be described. For example, the hematocrit value can be obtained by substituting the peak value, which is obtained in step S5, into a formula (1) below.

$$Y = aX + b \quad (1)$$

hematocrit value: Y
peak value: X
a, b: predefined coefficients

Note that the formula is not limited to the formula (1) described above. For example, not only a linear expression such as the formula (1) described above, but also a high order expression can be used.

The hematocrit value corresponding to the peak value can also be determined by recording an operation table in advance and referring to that table, instead of using a formula. An example of the table that indicates a correspondence relationship between the peak value and the hematocrit value is shown below.

TABLE 1

| Peak current value [μA] | Hematocrit value [%] |
|---|---|
| 1.50 | 100 |
| 8.88 | 80 |
| 12.39 | 70 |
| 15.57 | 60 |
| 17.44 | 53 |
| 19.03 | 46 |
| 19.82 | 42 |
| 20.70 | 38 |
| 22.26 | 30 |
| 24.14 | 20 |
| 25.84 | 10 |
| 27.35 | 0 |

The corrected value (e.g., glucose concentration value) that indicates the amount of the measuring target component, which has been corrected in step S6, is recorded in the recording unit 34, and displayed on the display screen 1c by the output unit 35 (step S7). The output unit 35 can also send the value to other apparatuses over a wired or wireless network.

As described above, in the example shown in FIG. 12, after the processing for measuring the response to the first signal (steps S2 and S3) has been ended, the processing for measuring the response to the second signal (steps S4 and S5) is executed. This is an example in the case where the first signal and the second signal are applied to a biological fluid for respective time periods that are not the same. In this case, there is no need to synchronize the first signal and the second signal, and therefore the processing and the configuration of the apparatus can be simplified.

Figure 13:
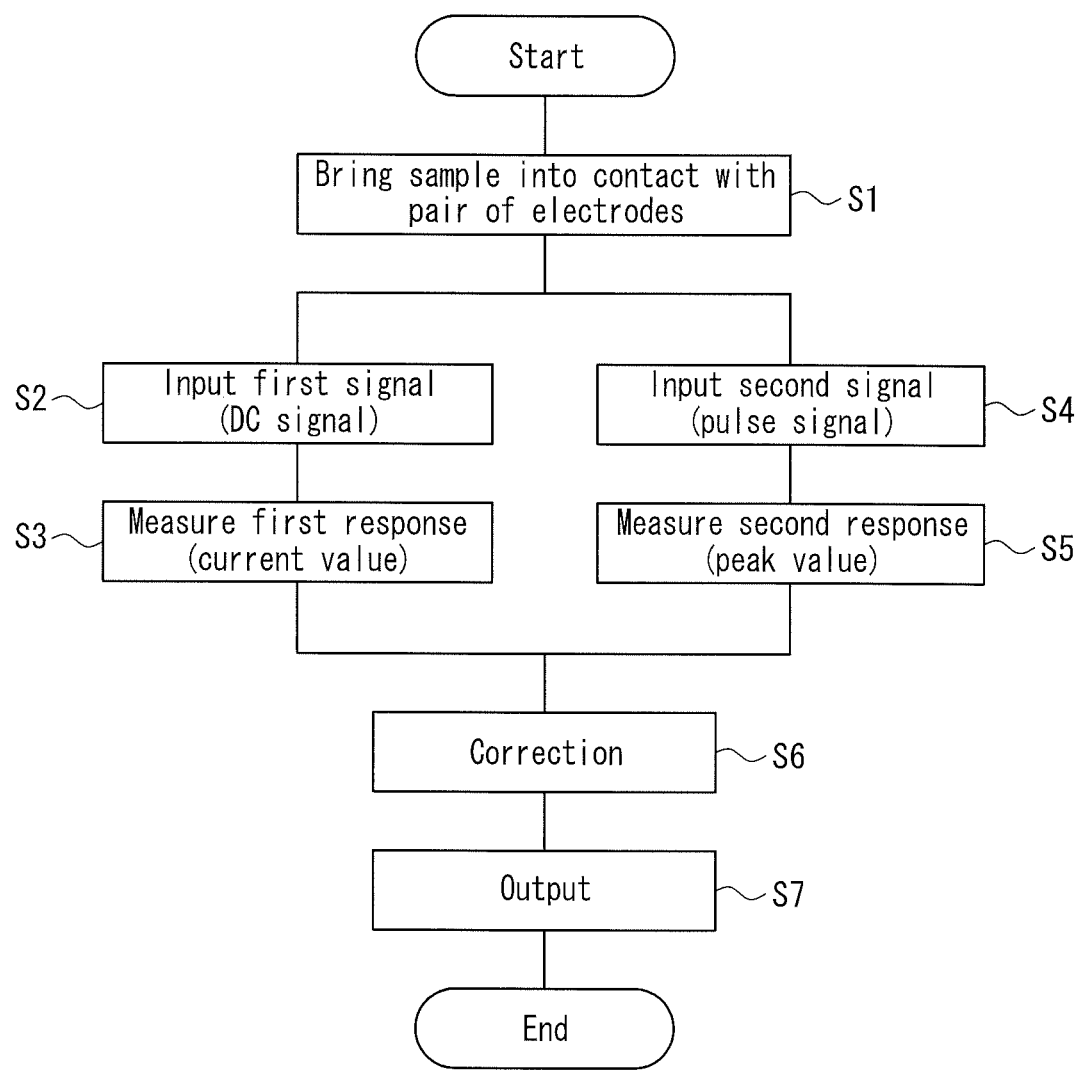
FIG. 13 is a flowchart illustrating another example of the operation of the measuring apparatus according to Embodiment 1.

FIG. 13 is flowchart illustrating another example of the operation of the blood glucose meter 1 according to this embodiment. In the example shown in FIG. 13, the processing for measuring the response to the first signal (steps S2 and S3) and the processing for measuring the response to the second signal (steps S4 and S5) are executed concurrently. Accordingly, the time required for the measurement can be reduced. Note that the details of the processing in steps S1 to S7 can be the same as the details of the processing in steps S1 to S7 of FIG. 12.

As described above, the measuring apparatus of this embodiment measures the component of the sample that reacts with the reagent based on the first electric response to the first signal that is applied to the first electrodes on which the reagent is provided. Furthermore, the measuring apparatus acquires the value for correcting this measurement result based on the peak value of the response signal with respect to a change in the level of the second signal that is applied to the second electrodes on which the reagent is not provided. This configuration makes it possible to improve the measurement accuracy with a simple configuration and processing. When compared with the case where, for example, in order to obtain the value for correcting the measured component, a composite signal containing, for example, DC and AC components is applied to a single pair of electrodes to obtain the value from response signals with respect to the DC component and the AC component, this embodiment can improve the measurement accuracy with simple processing and configuration because the component that reacts with the reagent is detected based on the first electric response, and the peak value is acquired based on the second electric response. Moreover, even when compared with the case where the measurement accuracy is achieved by applying a DC signal and an AC signal to two pairs of electrodes, respectively, at the same time and using the respective response signals, this embodiment can improve the measurement accuracy with simple processing and configuration because there is no need to deal with a DC signal and an AC signal at the same time.

Example of Configuration of Sensor 2

Next, the analytical device 2 of this embodiment will be specifically described with reference to FIGS. 14 to 17.

Figure 14:
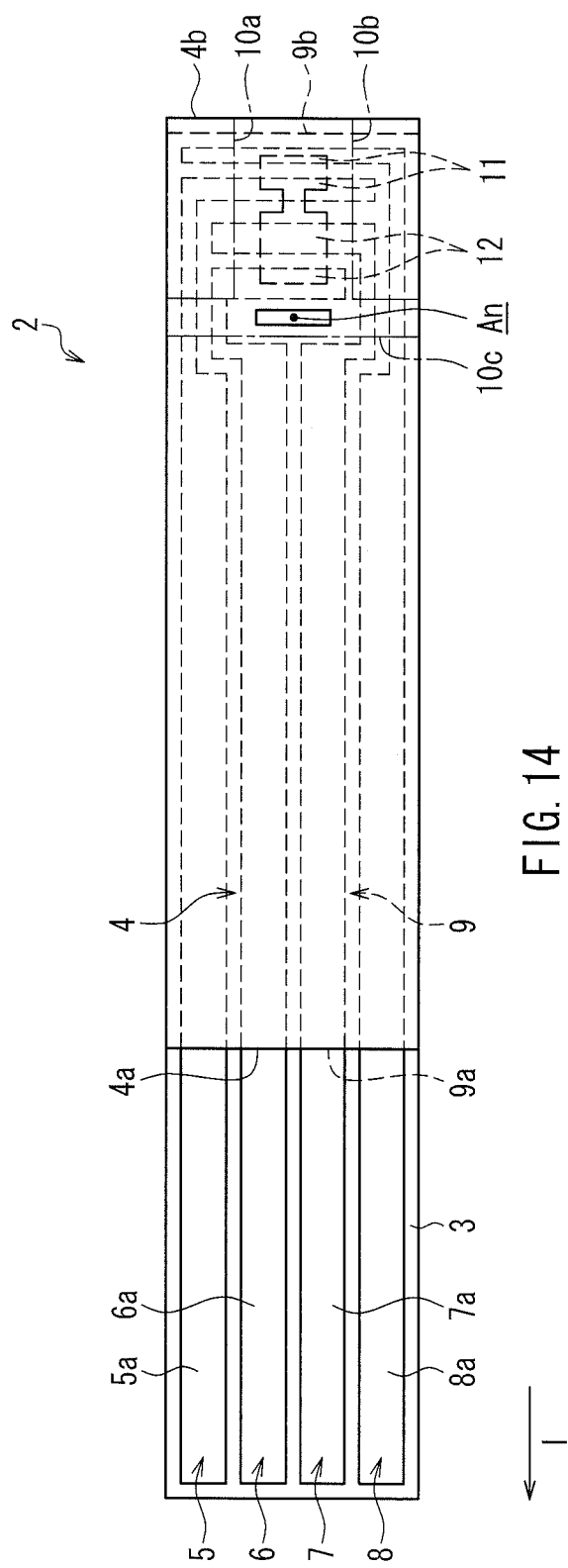
FIG. 14 is a plan view for explaining the analytical device shown in FIG. 1.
Figure 15:
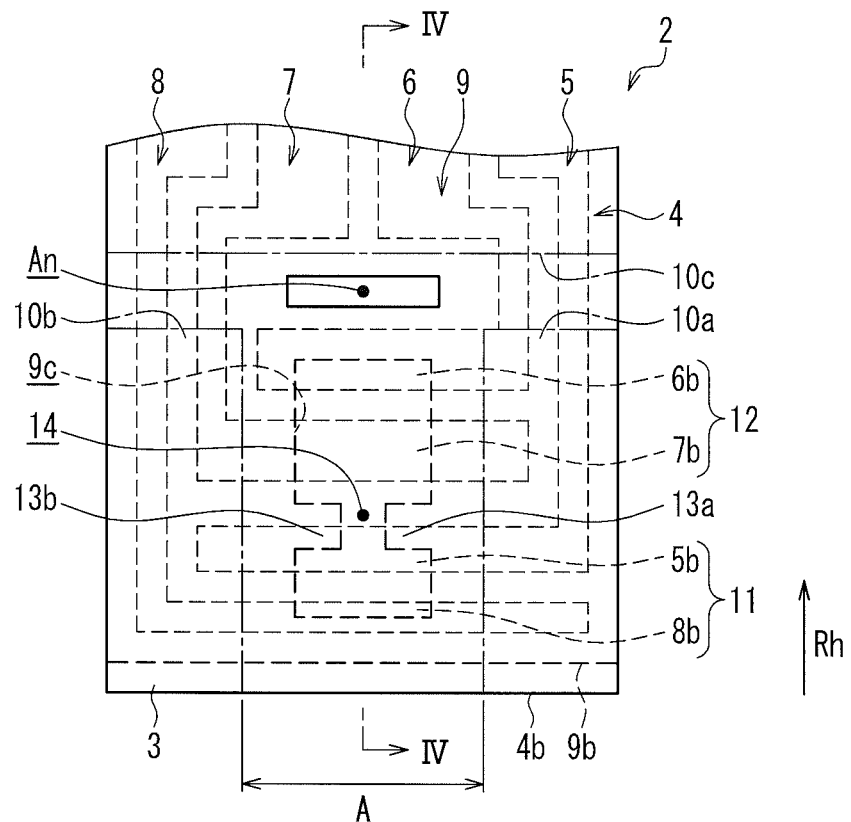
FIG. 15 is an enlarged plan view for explaining the configuration of a portion of the analytical device on the side of a blood introduction hole.
Figure 16:
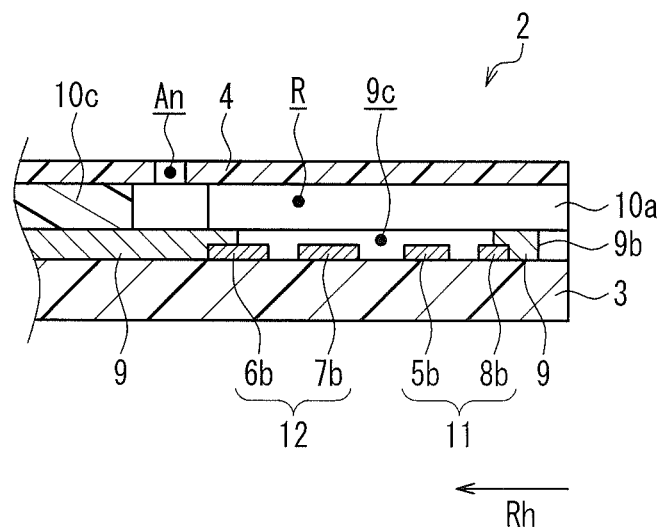
FIG. 16 is a cross-sectional view taken along line IV-IV in FIG. 15.
Figure 17:
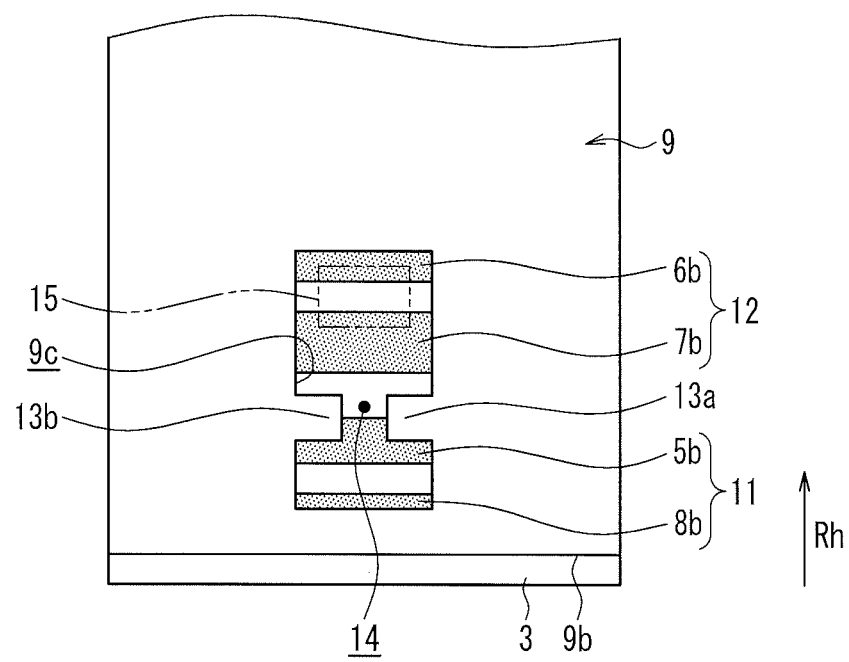
FIG. 17 is an enlarged plan view for explaining the configuration of a relevant portion of the analytical device.

FIG. 14 is a plan view for explaining the analytical device shown in FIG. 1. FIG. 15 is an enlarged plan view for explaining the configuration of a portion of the above-described analytical device on the side of a blood introduction hole. FIG. 16 is a cross-sectional view taken along line IV-IV in FIG. 15. FIG. 17 is an enlarged plan view for explaining the configuration of a relevant portion of the above-described analytical device.

Referring to FIG. 14, in the analytical device 2 of this embodiment, a substrate 3 and an opposing substrate 4 that is provided opposite the substrate 3 with a resist ink 9 being interposed between the two substrates are provided. As will be described in detail later, an introduction hole from which blood is introduced is provided at a right end portion of this analytical device 2 in FIG. 14. Moreover, the analytical device 2 is adapted to be inserted into the insertion port 1b (FIG. 1) of the blood glucose meter 1 in the direction of arrow "I" in FIG. 14.

For example, a hydrophobic synthetic resin may be used for the substrate 3. Four signal lines 5, 6, 7, and 8 are formed on the substrate 3. For example, carbon ink may be used for these signal lines 5, 6, 7, and 8. These signal lines 5, 6, 7, and 8 are formed in a predetermined pattern on the substrate 3 by screen printing, for example. Specifically, the signal lines 5, 6, 7, and 8 have linear wiring portions 5a, 6a, 7a, and 8a having the same width and electrode portions 5b, 6b, 7b, and 8b (FIG. 15) that are bent at right angles to the respective wiring portions 5a, 6a, 7a, and 8a.

Note that instead of the configuration described above, the signal lines 5, 6, 7, and 8 may also be formed using a thin metal film, for example.

Also, in the analytical device 2, as shown in FIG. 14, a left end portion (insertion portion) of the substrate 3 is not covered by the opposing substrate 4 and the resist ink 9, so that left end portions of the above-described wiring portions 5a, 6a, 7a, and 8a are exposed. The analytical device 2 is thus configured such that when the analytical device 2 is inserted into the insertion port 1b, the left end portions of the respective wiring portions 5a, 6a, 7a, and 8a are connected to a connecting unit (not shown) provided inside the main body 1a (FIG. 1) of the blood glucose meter 1, allowing the analytical device 2 to exchange voltage signals with the blood glucose meter 1.

Also, in the analytical device 2, as shown in FIG. 14, a pair of hematocrit electrodes 11 and a pair of glucose electrodes 12 are provided in a right end portion (sample inlet portion) of the analytical device 2, so that blood introduced into the analytical device 2 from the introduction hole travels along the flow path, which will be described later, and reaches the hematocrit electrodes 11 and the glucose electrodes 12.

For example, a hydrophilic synthetic resin may be used for the opposing substrate 4. A left end (insertion-side end portion) 4a of the opposing substrate 4 is positioned such that the left end portions of the respective wiring portions 5a, 6a, 7a, and 8a are exposed as described above. On the other hand, a right end (sample inlet-side end portion) 4b of the opposing substrate 4 is configured so as to coincide with a right end of the analytical device 2 (i.e., right end of the substrate 3). The hydrophilicity of the opposing substrate 4 allows blood traveling along the above-described flow path to readily reach the pair of glucose electrodes 12, which are provided on the downstream side with respect to an inflow direction of the blood. Furthermore, a vent An communicating with the flow path is formed in the opposing substrate 4, so that blood (sample) can smoothly flow into the flow path.

For example, an insulator such as thermosetting ink may be used for the resist ink 9. The resist ink 9 is formed in a predetermined pattern on the substrate 3 and on the signal lines 5, 6, 7, and 8 by screen printing, for example. More specifically, a left end 9a of the resist ink 9 is configured so as to coincide with the left end 4a of the opposing substrate 4. On the other hand, as shown in FIG. 14, a right end 9b of the resist ink 9 is configured so as to be located slightly to the left of the right end 4b of the opposing substrate 4. Since an insulator is used for the resist ink 9, the signal lines 5, 6, 7, and 8 are not adversely affected, and hence the measurement accuracy are not adversely affected.

Rectangular double-sided adhesive tapes 10a, 10b, and 10c are provided on the resist ink 9 such that the double-sided adhesive tapes 10a, 10b, and 10c are interposed between the resist ink 9 and the opposing substrate 4. The double-sided adhesive tapes 10a, 10b, and 10c serve as an adhesive layer for making the substrate 3 and the opposing substrate 4 adhere to each other and is adapted to make the substrate 3 and the opposing substrate 4 adhere to each other via the resist ink 9, which is formed on the substrate 3. Note that a double-sided adhesive tape having the same width as the substrate 3, the opposing substrate 4, and the resist ink 9 is used as the double-sided adhesive tape 10c, and one end (left end in FIG. 14) of the double-sided adhesive tape 10c coincides with the left end 4a of the opposing substrate 4 and the left end 9a of the resist ink 9. The aforementioned vent An is formed in the opposing substrate 4 at a position between the other end (right end in FIG. 14) of the double-sided adhesive tape 10c and the double-sided adhesive tapes 10a and 10b.

Note that instead of the configuration described above, the resist ink 9 may also be formed using an ultraviolet-curing resin, for example.

In the analytical device 2 of this embodiment, as indicated by "A" in FIG. 15, the blood introduction hole is formed at a lower end portion of the analytical device 2. The opening of this introduction hole is defined by the substrate 3, the opposing substrate 4, the resist ink 9, and the double-sided adhesive tapes 10a and 10b. A blood flow path R is formed inside the analytical device 2, extending from the opening toward the upper side in FIG. 15 (see also FIG. 16). Blood flows into this flow path R from the introduction hole in the inflow direction indicted by "Rh" in FIGS. 15 and 16 by capillary action. Note that in order to facilitate this capillary action, the above-described vent An is formed in the opposing substrate 4.

That is to say, in the analytical device 2 of this embodiment, the substrate 3, the opposing substrate 4, the resist ink (insulator) 9, and the double-sided adhesive tapes (adhesive layer) 10a, 10b, and 10c constitute a defining element that defines the flow path R of blood (sample). The length of the flow path R may be set at, for example, 1.1 to 10 mm, 1.5 to 4.5 mm, or 2 to 4 mm. The width of the flow path R may be set at, for example, 1 to 10 mm, 2 to 3.5 mm, or 1.5 to 2.5 mm. Furthermore, the capacity of the flow path R may be set at, for example, 0.1 to 10 µL, 0.15 to 0.5 µL, or 0.25 to 0.35 µL.

Also, in the flow path R, as shown in FIGS. 15 to 17, a cutout portion 9c is formed in the resist ink 9. Also, in the flow path R, the pair of hematocrit electrodes 11, which are a first pair of electrodes, are provided so as to be located on an upstream side (introduction hole side) in the flow path R, and the pair of glucose electrodes 12, which are a second pair of electrodes, are provided so as to be located downstream of the pair of hematocrit electrodes 11.

Specifically, the pair of hematocrit electrodes 11 are substantially constituted by those portions of the electrode portions 5b and 8b that are exposed in the cutout portion 9c. At the pair of hematocrit electrodes 11, in a state in which the above-described exposed portions of the electrode portions 5b and 8b are in contact with blood, a voltage signal based on an alternating voltage (AC) or a direct voltage (DC) is supplied to the signal lines 5 and 8, and thus the hematocrit value is detected by the blood glucose meter 1.

The pair of glucose electrodes 12 are substantially constituted by those portions of the electrode portions 6b and 7b that are exposed in the cutout portion 9c. Also, a solidified dropped reagent 15 is placed on the pair of glucose electrodes 12 as shown by a chain double-dashed line in FIG. 17. At the pair of glucose electrodes 12, in a state in which the above-described exposed portions of the electrode portions 6b and 7b and the dropped reagent 15 are in contact with blood, and the blood reacts with the dropped reagent 15, a voltage signal based on an alternating voltage (AC) or a direct voltage (DC) is supplied to the signal lines 6 and 7, and thus, the glucose level (blood glucose level) is detected by the blood glucose meter 1. In the measuring apparatus 1, the detected glucose level is corrected using the detected hematocrit value, and the corrected glucose level is treated as measurement data.

In the manufacturing process of the analytical device 2, before the opposing substrate 4 and the substrate 3 are bonded together, the reagent 15 in a liquid state is dropped on the pair of glucose electrodes 12 by an apparatus for ejecting a fixed amount of liquid, such as a dispenser, and the dropped reagent 15 is dried and thus solidified on the glucose electrodes 12.

Also, in the flow path R, as illustrated in FIG. 17, dropped reagent restricting elements 13a and 13b that restrict the movement of the dropped reagent 15 in the liquid state are provided between a downstream end portion of the pair of hematocrit electrodes 11 and an upstream end portion of the pair of glucose electrodes 12. The dropped reagent restricting elements 13a and 13b are formed integrally with the resist ink (defining element) 9. As shown in FIG. 17, the dropped reagent restricting elements 13a and 13b are formed on the electrode portion 5b of one of the pair of hematocrit electrodes 11. More specifically, a portion of each of the dropped reagent restricting elements 13a and 13b is provided so as to be overlaid on a portion of the electrode portion 5b, and the other portion of each of the dropped reagent restricting elements 13a and 13b is provided between the downstream end portion of the pair of hematocrit electrodes 11 and the upstream end portion of the pair of glucose electrodes 12.

Also, in the flow path R, as illustrated in FIG. 17, the dropped reagent restricting elements 13a and 13b and a gap 14 are provided in a crosswise direction that crosses the inflow direction Rh of blood (e.g., orthogonal direction that is orthogonal to the inflow direction Rh). That is to say, in the flow path R, the gap 14 is formed between the two dropped reagent restricting elements 13a and 13b.

In the analytical device 2 of this embodiment configured as described above, the dropped reagent restricting elements 13a and 13b are formed between the downstream end portion of the pair of hematocrit electrodes (first pair of electrodes) 11 and the upstream end portion of the pair of glucose electrodes (second pair of electrodes) 12 in the flow path R. Furthermore, in the analytical device 2 of this embodiment, in the flow path R, the dropped reagent restricting elements 13a and 13b and the gap 14 are provided in the crosswise direction that crosses the inflow direction Rh of blood (sample). Thus, unlike the above-described conventional example, the analytical device 2 of this embodiment can allow blood to sufficiently reach as far as the pair of glucose electrodes 12, which are provided on the downstream side in the flow path R.

Also, according to this embodiment, since the dropped reagent restricting elements 13a and 13b are formed on the pair of hematocrit electrodes 11, a sufficient amount of the reagent 15 can be dropped on the pair of glucose electrodes 12. Also, the dropped reagent restricting elements 13a and 13b can reliably restrict the movement of the dropped reagent 15. That is to say, the dropped reagent restricting elements 13a and 13b can reliably suppress the movement of the dropped reagent 15 to the side of the pair of hematocrit electrodes 11.

Also, according to this embodiment, since the dropped reagent restricting elements 13a and 13b are formed integrally with a portion of the resist ink (defining element) 9, it is possible to easily construct an analytical device 2 having a small number of components and a simple structure.

Also, according to this embodiment, since the dropped reagent restricting elements 13a and 13b are made of an insulator, it is possible to easily construct an analytical device 2 that is easy to manufacture.

Also, according to this embodiment, the opposing substrate 4, which is provided opposite the substrate 3, and the double-sided adhesive tapes (adhesive layer) 10a, 10b, and 10c for making the substrate 3 and the opposing substrate 4 adhere to each other are provided, and the defining element includes the resist ink (insulator) 9, which is provided on the substrate 3, the double-sided adhesive tapes 10a, 10b, and 10c, and the opposing substrate 4. Thus, according to this embodiment, it is possible to easily construct a low-cost analytical device 2 having a simple structure and a reduced thickness.

A method for manufacturing the analytical device 2 of this embodiment includes a first electrode pair forming step of forming the pair of hematocrit electrodes (first pair of electrodes) 11 on the substrate 3, the pair of hematocrit electrodes (first pair of electrodes) 11 being provided on the upstream side in the flow path R, a second electrode pair forming step of forming the pair of glucose electrodes (second pair of electrodes) 12 on the substrate 3, the pair of glucose electrodes (second pair of electrodes) 12 being provided on the downstream side in the flow path R, and a dropped reagent restricting element forming step of forming the dropped reagent restricting elements 13a and 13b, which restrict the movement of the dropped reagent 15, such that the gap 14 is created in the crosswise direction that crosses the inflow direction Rh of blood (sample) in the flow path R, the gap 14 being located between the downstream end portion of the pair of hematocrit electrodes 11 and the upstream end portion of the pair of glucose electrodes 12. Thus, according to the method for manufacturing the analytical device 2 of this embodiment, the dropped reagent restricting elements 13a and 13b and the gap 14 are formed between the downstream end portion of the pair of hematocrit electrodes 11 and the upstream end portion of the pair of glucose electrodes 12 in the flow path R by the dropped reagent restricting element forming step. As a result, according to the method for manufacturing the analytical device 2 of this embodiment, it is possible to manufacture an analytical device 2 that can allow blood to sufficiently reach as far as the pair of glucose electrodes 12, which are provided on the downstream side in the flow path R.

Also, according to the method for manufacturing the analytical device 2 of this embodiment, since the dropped reagent restricting elements 13a and 13b are formed on the pair of hematocrit electrodes 11 in the dropped reagent restricting element forming step, a sufficient amount of reagent 15 can be dropped on the pair of glucose electrodes 12.

Also, according to the method for manufacturing the analytical device 2 of this embodiment, in the first and second electrode pair forming steps, the pair of hematocrit electrodes 11 and the pair of glucose electrodes 12 are simultaneously formed on the substrate 3 using screen printing. Thus, according to this embodiment, the pair of hematocrit electrodes 11 and the pair of glucose electrodes 12 can be formed with high precision in a short period of time.

Also, according to this embodiment, the use of the analytical device 2 that can allow blood (sample) to sufficiently reach as far as the pair of glucose electrodes (second pair of electrodes) 12, which are provided on the downstream side in the flow path R, makes it possible to easily construct a blood glucose meter (measuring apparatus) 1 capable of performing an accurate measurement with respect to the blood.

The use of the analytical device 2 as described above, the analytical device 2, which has the first pair of electrodes (glucose electrodes) on which a sufficient amount of reagent is provided and the second pair of electrodes (hematocrit electrodes), as the sensor 2 of the blood glucose meter 1 shown in FIG. 2 can improve the measurement accuracy even more. Thus, the effect of improving the measurement accuracy with simple processing and configuration can be enhanced even more. Note that the analytical device 2 that can be used in the blood glucose meter 1 is not limited to the example described above.

Embodiment 2

Figure 18:
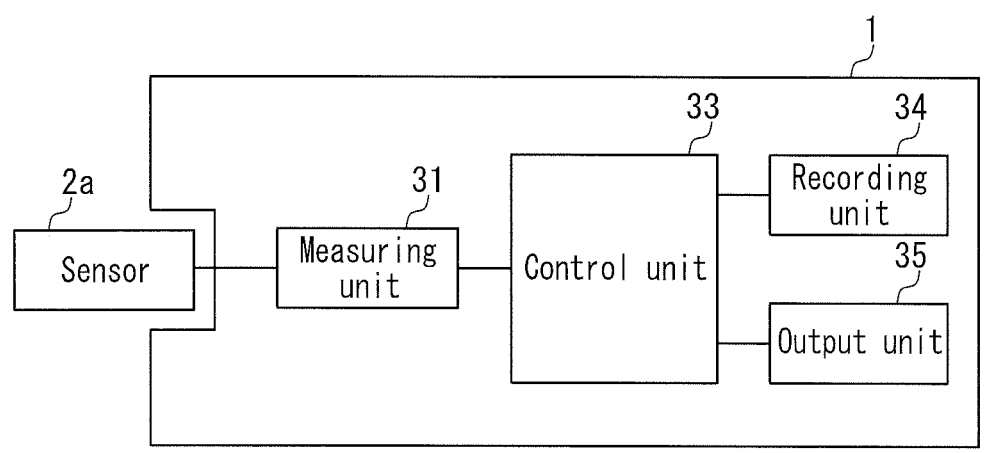
FIG. 18 is a block diagram showing an example of the configuration of a measuring apparatus according to Embodiment 2.

FIG. 18 is a block diagram showing an example of the configuration of a measuring apparatus according to Embodiment 2. A measuring apparatus 1a shown in FIG. 18 is an example of the measuring apparatus for measuring a hematocrit value of a blood sample. The measuring apparatus 1a includes a measuring unit 31, the control unit 33, the recording unit 34, and the output unit 35. Also, the measuring apparatus 1a is adapted so that the sensor 2 can be inserted into the measuring apparatus 1a, and a signal can be input to the electrodes of the inserted sensor 2.

The measuring unit 31 inputs a signal to the pair of electrodes of the sensor 2 that can come into contact with the blood sample and measures an electric response to the input signal. Here, as in the case of Embodiment 1, a signal that changes its value from a first level to a second level and then maintains the second level for a certain period of time can be used as the signal to be input. Also, the measuring unit 31 measures the electric response to this input signal as the peak value of the response signal with respect to the change in the input signal.

The control unit 33 determines the hematocrit value of the blood sample from the peak value that is measured by the measuring unit 31. For example, the same processing as that of Embodiment 1 described above can be used as the processing for determining the hematocrit value from the peak value. An apparatus for measuring the hematocrit value of a blood sample as described above is also one of embodiments of the invention. Also, this embodiment can be applied as an apparatus exclusively for measurement of the hematocrit value.

Effects of Embodiments and Variations

In Embodiments 1 and 2 described above, attention is paid to the peak value of the response signal with respect to the change in the level of the input signal, and an input signal having a waveform that is preferred in order to generate the peak value with high accuracy is used. For this reason, according to Embodiments 1 and 2 described above, a measurement can be made with only the current value, and therefore the system can be simplified. Moreover, the amount of a specific component of the sample can be judged with an input waveform having at least one step, at a time point when the signal level becomes constant after that step (e.g., rising edge). Therefore, the measuring method can be simplified, and the measurement time can be reduced. Moreover, in Embodiments 1 and 2 described above, it is not necessary to input a signal having a repeated waveform like a sine wave as the input signal, nor to input a signal having AC components of a plurality of frequencies. Furthermore, in Embodiments 1 and 2 described above, it is not necessary to measure the admittance and the phase information as the response to an input signal having an AC component, and therefore the apparatus and the processing can be simplified.

In Embodiment 1 described above, an example in which the sample is blood, and glucose and hematocrit are measured based on the response to the first signal and the response to the second signal, respectively, has been described. However, the sample and the measuring target component are not limited to the above-described example. Various other biological fluids can be used as the sample of the invention. For example, a configuration may also be adopted in which lactic acid is measured as the measuring target component instead of glucose, and a lactic acid value obtained from the first electric response is corrected using the hematocrit value. Moreover, the invention can also be applied to other measurement systems having the hematocrit correction function. Moreover, the measurement using the peak value of the response signal according to Embodiments 1 and 2 described above can also be applied to, for example, electrolyte and pH testing of a blood specimen, blood coagulation monitoring (thrombotic risk assessment), control solution detection, or other measurements, instead of the measurement of the hematocrit value. In addition, the measuring method and the measuring apparatus according to the above-described embodiments can be used for measurement of a component that is correlated with a peak value of a response signal with respect to a change in an input signal.

The embodiments described above are to be considered in all respects as illustrative and not restrictive. The scope of the invention is indicated by the appended claims rather than by the foregoing description, and all changes which come within the meaning and range of equivalency of the claims are therefore intended to be embraced therein.

What is claimed is:

1. A method for measuring glucose concentration in a blood sample, the method comprising the steps of:
    introducing the sample to a measuring apparatus comprising a first measuring unit, a second measuring unit and a control unit;
    applying a first signal to the sample in a state in which the sample is reacted with a reagent;
    measuring via the first measuring unit a first electric response of the sample to the first signal to obtain a glucose concentration value;
    applying a single second signal to the sample in a state in which the sample is not reacted with the reagent, the second signal changing its value from a first level to a second level and thereafter maintaining the second level for a certain period of time;
    measuring via the second measuring unit a second electric response of the sample to the single second signal as a peak value of a response signal caused by the change in the second signal from the first level to the second level; and determining via the control unit a hematocrit value of the sample based on the peak value of the second electric response by referring to a correspondence relationship between the peak value and the hematocrit value.

2. The measuring method according to claim 1, wherein the second signal contains a rectangular wave or trapezoidal wave component as a waveform in which the second signal changes its value from the first level to the second level and thereafter maintains the second level for a certain period of time.

3. The measuring method according to claim 1, wherein a time it takes for the second signal to change its value from the first level to the second level is 30 μs or shorter than 30 μs.

4. The measuring method according to claim 1, wherein a time it takes for the second signal to change its value from the first level to the second level is 7 μs or shorter than 7 μs.

5. The measuring method according to claim 1, wherein a time it takes for the second signal to change its value from the first level to the second level is 2 μs or shorter than 2 μs.

6. A measuring apparatus comprising:
a first measuring unit for measuring a first electric response to a first signal applied to a blood sample to obtain a glucose concentration value;
a second measuring unit for measuring a second electric response to a second signal applied to the sample, where the second signal changes value from a first level to a second level and thereafter maintains at the second level for a certain period of time, and where the second electric response is measured as a peak value of a response signal with respect to the change in the second signal from the first level to the second level; and
a control unit for determining a hematocrit value of the sample, based on the peak value of the second electric response by referring to a correspondence relationship between the peak value and the hematocrit value.

7. The measuring apparatus according to claim 6, wherein the first signal is applied to the sample in a state in which the sample is reacted with a reagent; and
the second signal is applied to the sample in a state in which the sample is not reacted with the reagent.

8. The measuring apparatus according to claim 6, wherein the sample is present on a sensor comprising a first pair of electrodes on which a reagent is provided and which are located in a flow path of the sample; and a second pair of electrodes on which the reagent is not provided and which are also located in the flow path of the sample.

* * * * *